United States Patent [19]

Vaya et al.

[11] Patent Number: 4,889,929
[45] Date of Patent: Dec. 26, 1989

[54] PREPARATION OF 1'-ETHOXYCARBONYL-OXYETHYL ESTERS OF PENICILLINS

[75] Inventors: Jacob Vaya; David Ladkani; Clara Schoenberger, all of Jerusalem; Joseph Kaspi, Givatayim; Gad Salemnick, Jerusalem; Haim Yellin, Ramat-Gan; Stephan Cherkez, Ramat-Gan, all of Israel

[73] Assignee: Astra Lakemedel Aktiebolag, Sodertalje, Sweden

[21] Appl. No.: 30,280

[22] Filed: Mar. 26, 1987

Related U.S. Application Data

[63] Continuation of Ser. No. 543,252, Oct. 19, 1983, abandoned.

[30] Foreign Application Priority Data

Jan. 7, 1983 [IL] Israel ............................ 67637

[51] Int. Cl.$^4$ ............................ C07D 499/08
[52] U.S. Cl. .................... 540/318; 540/336; 540/338
[58] Field of Search .................. 540/318, 336, 338

[56] References Cited

U.S. PATENT DOCUMENTS 3,697,507  10/1972  Fredericksen et al. ............. 540/336
3,873,521   3/1975  Ekstrom et al. .................... 540/336
4,342,772   8/1982  Godtfredsen et al. .......... 540/336 X

FOREIGN PATENT DOCUMENTS 187312  4/1978  Czechoslovakia .

Primary Examiner—Werren B. Lone
Assistant Examiner—Vera C. Clarke
Attorney, Agent, or Firm—M. Andrea Ryan

[57] ABSTRACT

Process for the preparation of 1'-ethoxy carbonyloxy ethyl esters of penicillins, wherein a compound of the formula

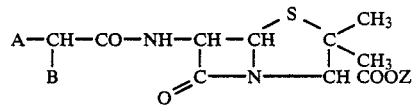

in which A is phenyl, phenoxy or 4-hydroxyphenyl, B is hydrogen, an amino group or a protected amino group and Z is hydrogen or a cation selected from the group of alkali metal, tri (lower alkyl) ammonium and tetra (lower alkyl) ammonium, is reacted with 1-bromoethyl ethyl carbonate in an organic solvent and when B is a protected amino group the protecting group is split off to yield a primary amino group.

There are also provided novel compounds of the formula

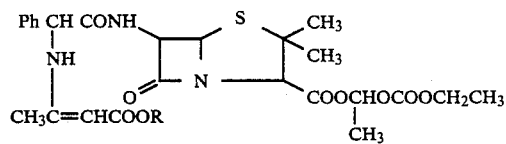

in which Ph is phenyl and R is $CH_3$— or $C_2H_5$—.

4 Claims, No Drawings

PREPARATION OF 1'-ETHOXYCARBONYL-OXYETHYL ESTERS OF PENICILLINS

This application is a continuation of application Ser. No. 543,252, filed on Oct. 19, 1983, now abandoned.

This invention relates to a process for the preparation of 1'-ethoxy carbonyloxy ethyl ester of penicillins, in which a new potent esterification agent is used. These esters, used as antibiotic pro-drugs, are produced in better yields and higher purity than known before.

Ampicillin, which is D(−) α-amino benzyl penicillin, is an effective broad spectrum antibiotic drug, especially against Gram-positive bacteria. It is widely used all over the world, as a human and veterinary drug. Ampicillin is administered orally, due to its relative stability in the gastric fluids. Absorption of ampicillin from the gastrointestinal tract, however, is far from being complete. Substantial amount of drug does not reach the blood stream. Larger doses are thus required in order to achieve therapeutical levels in the body.

A solution to this problem is to modify the ampicillin molecule in order to enhance its absorption. One way of doing it is by esterifying the carboxylic group of ampicillin. Absorption of ampicillin esters was found to be much better than the parent compound. Several esters, which are well absorbed, and split off readily the esterifying group in the blood stream, were discovered. As a result, an almost quantitative absorption of ampicillin is achieved. Some of these ampicillin esters are marketed as human drugs.

Bacampicillin, which is the 1'-ethoxy carbonyloxy ethyl ester of ampicillin (marketed as the hydrochloride) (formula I):

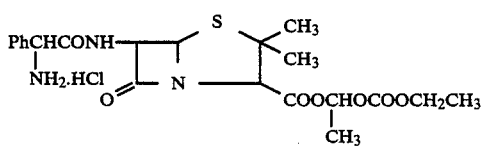

is being successfully used as an antibacterial drug. It is characterized by an almost quantitative absorption from the digestive tract to the blood stream, and a good tolerance by the gastro-intestinal system. Bacampicillin was first disclosed in British Pat. No. 1,363,506.

It is the object of this invention to provide a novel esterification agent for the preparation of bacampicillin and similar drugs.

Another object of this invention is to improve the existing processes for the preparation of bacampicillin. Using a new esterification agent, a marked improvement over the present know-how is established.

Still another object of this invention is the development of a new process for the preparation of bacampicillin. This process gives a product free from toxic contaminants present in the reported processes.

According to prior disclosures, bacampicillin was prepared in several ways. One process, disclosed in British Pat. No. 1,363,506, starts with potassium benzyl penicillinate (formula II), which is treated with 1-chloroethyl ethyl carbonate (CEC, formula III) in aqueous dioxane giving 1'-ethoxy carbonyloxyethyl benzyl penicillinate (formula IV) in less than moderate yields.

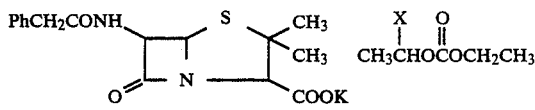

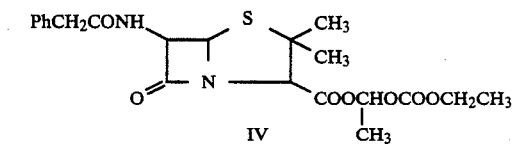

In these formulae X is Cl and Ph is phenyl.

The British patent mentions the esterification of penicillins with compounds of formula III in which X may be, among others, halogen and preferably chlorine or bromine. However, there is no specific disclosure of the use of 1-bromoethyl ethyl carbonate (BEC) nor is there any evidence that this compound has ever been obtained or used.

An improvement of the esterification reaction is disclosed in British Pat. No. 1,443,738 which consists in the use of an equivalent amount of a phase transfer catalyst such as tetrabutyl ammonium hydrogen sulfate. In the improved process reaction time was shorter and the yield improved. In the second step of the process, the amide group was cleaved, using first phosphorous pentachloride, then an alcohol and finally water. This reaction has to be carried out at sub-ambient temperatures (−30° C. or less). The product obtained is 1'-ethoxy carbonyloxy ethyl 6-amino penicillanate (formula V). This compound

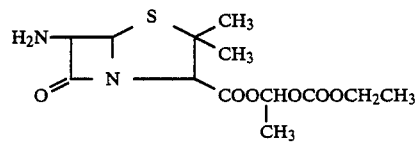

was acylated, using either D(−) phenyl glycyl-chloride hydrochloride or sodium (potassium) N-(1-methoxycarbonylpropen-2-yl)-D(−)-α-amino phenyl acetate, affording bacampicillin. In this process, benzyl penicillin is esterified by CEC and then the synthesis follows the known industrial processes for the manufacturing of ampicillin.

A second process involves compounds of formula VI, wherein E is an amino group or a group that can be converted to amino group.

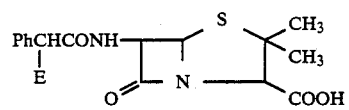

Such a compound is first esterified by CEC and then E is converted to amino group yielding bacampicillin. This process, taken as such, claims a very wide range of possible reactants for the preparation of bacampicillin. A closer look at British Pat. No. 1,363,506 reveals that, in the preparation of many esters of α-amino penicillins (including acampicillin), only one such method was employed where E=N₃. The α-azido penicillin was esterified with CEC. Hydrogenolysis of the azido penicillin ester gave the corresponding ampicillin ester, e.g. bacampicillin.

Another procedure (U.S. Pat. No. 4,072,677) claims the esterification of an N-protected ampicillin by CEC under phase transfer catalysis conditions, followed by removal of the protecting group.

In all the above mentioned processes, the esterification of the penicillin molecule was carried out by CEC. This is a known compound, first reported in the chemical literature in 1889. CEC is commercially available. From the family of 1-haloethyl ethyl carbonate (formula III), this was the only known compound.

The use of CEC for the esterification of penicillin has several drawbacks. The rate of the reaction with CEC is slow and as many as three equivalents of CEC are required. Moreover, drastic reaction conditions such as long reaction time, high temperatures and the use of catalysts such as phase transfer catalysts are required. When such drastic conditions are applied on sensitive compounds like penicillins, the inevitable consequence of degradation may occur. This causes reduced yields and impure products. Indeed, in all the processes for preparing bacampicillin, the yields are relatively low and many procedures give material of inferior quality.

It is also known that many chloro compounds are lachrymators and skin irritants. Any esters produced with CEC should be subjected to extensive and thorough purification operations to remove traces of CEC.

Because of the relative ability of a C—Br bond as compared to a C—Cl bond, it was to be expected that an esterification reaction would proceed much more smoothly with 1-bromoethyl ethyl carbonate (BEC) than with 1-chloroethyl ethyl carbonate (CEC), requiring less reagent, shorter reaction time, lower reaction temperature and no catalyst while at the same time producing better yields. Where the acid subjected to esterification is sensitive such as, for example, an acid of the α-aminopenicillin series, shortening of the reaction time and lowering the reaction temperature have favourable effects on the yield of the desired final product in that the degradation of the sensitive β-lactam moiety is minimized.

Thus, in view of all the various deficiencies of 1-chloroethyl ethyl carbonate, there has been a longfelt want to replace it by 1-bromoethyl ethyl carbonate (BEC), having the formula VII:

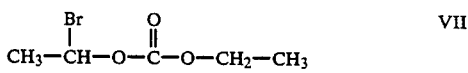

VII

However, BEC has never been reported in the chemical literature. Furthermore, published reports taught that bromination of diethylcarbonate or ethyl chloroformate, the two possible precursors for BEC, gave only degradation products. No BEC was obtained in these reactions.

BEC, which is a novel compound, can be prepared in several ways. One process comprises a free radical bromination of diethyl carbonate. The best way to initiate radical bromination is photochemically. Light (UV or visible) is irradiating the reaction mixture during the bromination. Bromination occurs predominantly in the o-position, leading to the formation of BEC. Other types of initiators can be used. Light can be substituted by a chemical radical source such as azo bis-(isobutyronitrile) or benzoyl peroxide. Radical bromination is not limited to bromine only. Other brominating agents, such as N-bromosuccinimide or 1,3-dibromo-5,5-dimethyl imidazolidinyl-2,4-dione, are also capable of brominating diethylcarbonate to give BEC. Another process involved the radical bromination of ethyl chloroformate to give 1-bromoethyl chloroformate. Bromination can be accomplished in variety of initiators and bromine sources in a parallel to bromination of diethyl carbonate. Further treatment of 1-bromoethyl chloroformate with ethanol yields. BEC Still another process is the substitution of chlorine by bromine in CEC. Suitable bromide salts which are soluble in polar aprotic solvents do it successfully.

BEC is a very potent esterification agent for the preparation of 1'-ethoxycarbonyloxy ethyl esters. It is especially useful when the esterification is carried out on salts of relatively unstable and sensitive acids. This is the case with most β-lactam antibiotics. The esters of benzyl penicillin and N-protected α-amino penicillins (ampicillin, amoxycillin) were prepared in excellent yields and high purity under mild conditions (low temperatures and short reaction time)

For example, according to British Pat. No. 1,363,506 1'-ethoxycarbonyloxyethyl benzyl penicillinate was prepared by reacting potassium benzyl penicillinate with CEC in aqueous dioxane at room temperature for 66 hours. The ester was obtained at 33% yield with an unspecified degree of purity. An improvement was reported later in British Pat. No. 1,443,738 according to which the rather expensive tetrabutyl ammonium benzyl penicillinate was prepared and this salt was then subjected to the esterification with CEC in boiling acetone for 6 hours The ester was obtained in an overall yield of 65% and in 90% purity.

An unexpected significant improvement has now been achieved in accordance with the present invention by using BEC instead of CEC for the esterification. Thus, potassium benzyl penicillinate was reacted with BEC in moist acetone at 40° C. for 5 hours to give 1'-ethoxycarbonyloxy ethyl benzyl penicillinate in a quantitative yield and 99% purity. This is a dramatic increase in yield and product quality using at the same time milder reaction conditions as shown in accordance with the present invention. The same improvements were observed in accordance with the invention in the eserification of other penicillins.

The product obtained from the esterification of potassium benzyl penicillinate with BEC gives a starting material for many 1'-ethoxycarbonyloxy ethyl esters of known semi-synthetic penicillins. Thus, the ester having formula IV was cleved by a known sequence of chemical reactions to afford the ester of 6-amino penicillinanic acid having formula V. Acylation of V with the appropriate agent affords the penicillin ester. Thus treating V with D(—) phenyl glycyl chloride hydrochloride gives bacampicillin (formula I), in good yields. The high purity of IV obtained from BEC gave bacampicillin in higher yields and better purity than reported before, when CEC was used.

The esterification of potassium benzyl penicillinate was carried out in non-hydroxylic polar solvents. Examples are acetone, 2-butanone, dimethylsulfoxide and acetonitrile. The preferred solvent is acetone. The reaction is best carried out in the presence of an acid absorber such as sodium bicarbonate. The temperature range for the reaction is between 20° to 50° but the range of 35°–45° is preferred. Reaction is best carried out in moist solvent (ca. 4% water) in order to accelerate the esterification (enhancing the solubility of the potassium salt). The reaction rate can also be accelerated by the addition of a catalytic amount of a quaternary ammonium salt such as tetrabutyl ammonium bromide, but the addition of such a salt is not an essential part of the invention.

A new process for the production of bacampicillin, using BEC as esterification agent, is another part of the invention.

Direct esterification of ampicillin by BEC gives bacampicillin in lower yield. The product is contaminated with several compounds of which one of the major contaminants is believed to be of the formula VIII.

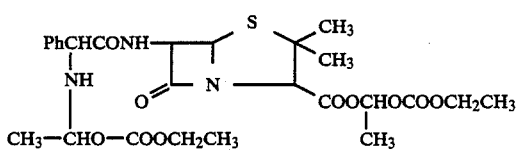

The presence of an amino group, another possible site for reaction, has to be avoided. As a result, the esterification has to be carried out on a derivative of ampicillin with a protected amino group. BEC will then react only with the carboxylic acid. After the esterification is complete, removal of the protecting group affords bacampicillin. The amino protecting group must be removed under very mild conditions, due to the sensitivity of the penicillin nucleus. Protecting groups usually employed in peptide chemistry are not suitable. They do not fulfill the condition of an easy removal. We found that protection in the form of enamine by reaction of ampicillin with alkyl acetoacetate is suitable. The protecting group is removed under mild acidic conditions. Any such compound of formula IX wherein M is sodium, potassium or tri (lower) alkyl ammonium cation and wherein $R_1$ is a methyl or ethyl group, will be referred to hereinafter as "ampicillin Dane salt".

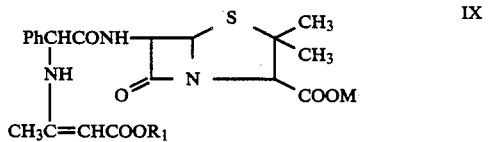

A solution of IX (M=HN(C$_2$H$_5$)$_3$; R$_1$=CH$_3$) is obtained easily by reacting ampicillin trihydrate with triethylamine and methylacetoacetate. The nature of the solvent is not so important. Acetone, dichloromethate, ethyl acetate, isopropanol, acetonitrile, and methyl acetoacetate are mere examples for suitable solvents. The reaction is carried out in the temperature range of 10°–50° preferably at 20–40°. Usually an excess of alkyl acetoacetate is used in order to achieve a complete protection of the amino group.

A crystalline potassium salt of IX (R$_1$=CH$_3$; M=K) can be prepared by treating a solution of IX with a potassium salt soluble is the organic solvent used. The other crystalline form of ampicillin, anhydrous ampicillin, reacts in the same way but much longer reaction time is needed due to lower dissolution rate.

Based on the foregoing observations and discoveries, the invention provides a process for the preparation of a 1'-ethoxycarbonyloxyethyl ester of a penicillin having the formula:

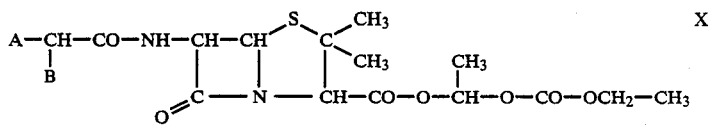

in which A is a phenyl group, phenoxy group or 4-hydroxyphenyl group and B is hydrogen, an amino group or a protected amino group, wherein a compound of the formula

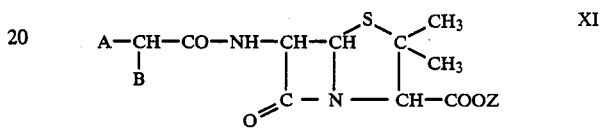

wherein A and B are as in formula X and Z is hydrogen or a cation selected from the group of alkali metal, tri (lower alkyl) ammonium and tetra (lower alkyl) ammonium, is reacted with 1-bromoethyl ethyl carbonate in an organic solvent and when B is a protected amino group the protecting group is split off to yield a primary amino group.

If desired, the reaction is carried out in the presence of an acid acceptor.

Also if desired the resulting ester may be subjected to treatment for splitting off the acyl residue

to yield 2-ethoxycarbonyloxyethyl ester of 6-amino penicillanic acid and the latter is then acylated with a different acyl group, as is known per se. In this way one 1'-ethoxycarbonyloxy ethyl ester of a semi-synthetic penicillin according to the invention may be converted into another by replacing the acyl residue.

By way of example, the reaction of penicillin G (formula II or the corresponding sodium salt) with BEC in acetone at 40° proceeds smoothly to give the ester having formula IV in quantitative yield and 99% pure. If desired, catalytic amounts of a tertiary amino or quaternary ammonium salt may be added, e.g. triethyl amine or tetrabutyl ammonium bromide. In this way the reaction may be accelerated.

In a similar manner salts of penicillin V (formula XI: A=phehoxy, B=hydrogen) react to give the corresponding ester (formula X: A=phenoxy, B=hydrogen).

These esters are a suitable source for the preparation of bacampicillin. Cleavage of the acyl group by known procedures (e.g. phosphorous pentachloride, alcohol and water) affords the ester of the formula V. This compound is acylated by an appropriate derivative of phenyl glycine to give bacampicillin.

Other suitable candidates for the preparation of bacampicillin are compounds having the formula IX. These compounds are esterified smoothly by BEC to give compounds having formula XIII

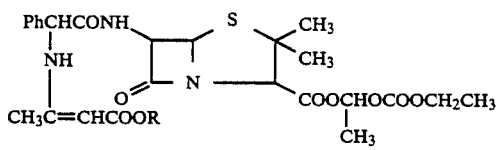

XIII in which Ph is phenyl and R is methyl or ethyl. This compound named bacampicillin Dane "salt" (BDS) yields bacampicillin upon treatment with dilute aqueous acid, e.g. hydrochloric acid.

ADS of formula XIII are novel compounds. When these compounds are obtained as intermediates in the preparation of bacampicillin they may or may not be isolated.

In a similar way the 1'-ethoxycarbonyloxy ethyl ester of amoxycillin can be prepared.

Preferably an excess of 30–120% of BEC is used for the esterification in order to complete the reaction. Usually, an excess of 50–100% of BEC is used. Under these conditions, esterification is complete within several hours. Excess of BEC is destroyed by water at room temperature. The N-protecting group is then removed by a careful addition of aqueous hydrochloric acid. Care must be taken during the acid addition lest the pH will drop too low. Making the solution too acidic results in partial decomposition of the penicillin. A final, stable pH of ca. 2.2 was found most satisfactory for complete removal of the N-protecting group while keeping the penicillin molecule intact.

The esterification can be carried out equally well on a solid ampicillin Dane salt or a solution of an ampicillin Dane salt. In the latter case the product obtained in the protection step is directly reacted with BEC. Usually ADS is also not isolated and a "one pot" process from ampicillin to bacampicillin is carried out.

The process according to the invention has several advantages over the known processes for the preparation of 7-ethoxycarbonyloxy esters of penicillins. Taking, for example, the case of bacampicillin, the new process gives bacampicillin in higher yield than disclosed before and of very good quality. The chemical operations needed to be executed in the process are simple. For instance there is no need to work at sub-ambient temperatures (−30° C. and below). The mild conditions of the process lead to minimal degradation of the sensitive β-lactam compounds. No toxic materials are involved in the process. In the known processes, conversion of IV to V necessitates the use of N,N-dimethylaniline or quinoline These are toxic materials and they should be removed. Their removal from the final product is very difficult. The present invention completely avoids the use of toxic compounds.

The invention is further illustrated by the following examples to which it is not limited. Examples 1 to 3 illustrate the preparation of 1 bromoethyl ethyl carbonate.

Preparation of 1-bromoethyl ethyl carbonate

EXAMPLE 1

A mixture of 354 g (3 mole) diethylcarbonate and 700 ml carbon tetrachloride was stirred and irradiated externally with a 1.5 kw iodine - quartz lamp. The heat from the lamp brought the mixture to reflux. Bromine (412.8 g, 2.58 mole) was added slowly through a dip-pipe below the surface of the mixture over a period of 15–17 hours at such a rate so as to keep the colour of the solution light red throughout the reaction. The temperature in the solution was 84°–85° C. Hydrogen bromide evolved copiously during the addition. The reaction mixture was cooled, washed with aqueous sodium bisulfite and dried over magnesium sulfate. Carbon tetrachloride was distilled at atmospheric pressure The rest was fractionally distilled at 30 mm Hg pressure. The first fraction consisted of unreacted diethylcarbonate, the second fraction boiled at 90°–95° (30 mm pressure) was 1-bromoethyl ethyl carbonate. The residue in the pot was mainly bis-(1-bromoethyl) carbonate. The yield was about 52% calculated on bromine.

The following physical data of 1-bromoethyl ethyl carbonate:

| | | | |
|---|---|---|---|
| Boiling point at 60 mm Hg - 110° | | | |
| Bromine content 40.6% (theoretical 40.61%) | | | |
| Density ($D^{20}_4$) | | | 1.4244 |
| Refractive index ($n^{20}_D$) | | | 1.4395 |
| NMR Spectrum | 1.4 | ppm 3H triplet | J = 7 Hz |
| | 2.0 | ppm 3H doublet | J = 6 Hz |
| | 4.25 | ppm 2H quartet | J = 7 Hz |
| | 6.6 | ppm 1H quartet | J = 6 Hz |

GC analysis showed it to be a pure compound.

EXAMPLE 2

848.2 g (7.18 mole) of diethyl carbonate and 420 ml 1,1,2-trichloro-trifluoro ethane ("Freon" 113 Trade Mark) were stirred and irradiated by a 150 w high pressure mercury immersion lamp. The mixture was heated by the lamp and soon began to boil at 75° . Bromine (936 g, 5.85 mole) was added slowly through a dip-pipe at such a rate to keep the solution lightly coloured. Addition took 4¼ hours. During the addition the temperature in the flask rose steadily from 75° to 94°. HBr evolved during the addition. The reaction was cooled to 40° and dry nitrogen was passed until fumes of HBr did no longer evolve. The reaction was subjected to fractional distillation as described above. The yield of isolated 1-bromoethyl ethyl carbonate was 62%.

EXAMPLE 3

585 g Diethylcarbonate (4.92 mole) was heated by an external 1500 w iodine quartz lamp. The mixture was allowed to reflux (temperature 125°) by the heat evolved from the lamp. 318.2 g (2.0 mole) of bromine is added slowly during 3 hours through a dip-pipe at such a rate that the solution colour was yellow to light orange. The temperature dropped to ca. 120° at the beginning of the addition, but rose again slowly. When all the bromine was consumed the temperature was 137°. The reaction mixture was cooled and treated as described in Example 2. Fractional distillation afforded 1-bromoethyl ethyl carbonate in a 68.5% yield. The earlier fraction contained about 6.5% more of 1-bromoethyl ethyl carbonate.

EXAMPLE 4

A mixture of potassium benzyl penicillinate (20 g), sodium bicarbonate (18.15 g), water (2.4 ml) and acetone (60 ml) was heated to 40° C. 1-Bromoethyl ethyl carbonate (21.2 g) was added during 30 minutes. The reaction mixture was stirred for 4.5 hours at 40°. Water (60 ml) was added and the reaction mixture stirred for 1 hour at ca. 30° C. Ethyl acetate (60 ml) was added and the mixture was filtered. The organic phase was separated and washed with a saturated sodium bicarbonate solution and 10% sodium chloride solution. The mixture was dried and the solvent evaporated under reduced pressure. 1′-Ethoxycarbonyloxyethyl benzyl penicillinate was obtained in quantitative yield and 99% purity (assayed by HPLC and mercurometric titration).

EXAMPLE 5

A mixture of potassium benzyl pencillinate (20 g), 1-bromoethyl ethyl carbonate (19.15 g), sodium bicarbonate (18.15 g), tetrabutyl ammonium bromide (1 g) and acetone (60 ml) was stirred at 45° C. for 2.5 hours. The mixture was treated in the same way as described in Example 1 to give 1′-ethoxycarbonyloxy ethyl benzyl penicillinate 97% pure, in quantitative yield.

EXAMPLE 6

1′-Ethoxycarbonyloxy ethyl benzyl penicillinate (100 g), obtained as described in the preceding examples, was dissolved in methylene chloride (375 ml). N,N-Dimethyl aniline (61 ml) was added and the mixture was cooled to −80° C. Phosphorous pentachloride was added in three portions of 31 g taking care that the temperature does not rise above −60° C. The mixture was stirred at −70° for 1½ hours. Cold methanol (140 ml) was added slowly keeping the temperature below −55° C. Stirring was continued at −70° C. for 2 hours. Water (500 ml) and petroleum ether (450 ml) were added and the phases separated. The organic layer was washed with water (500 ml). The combined aqueous fractions were combined and basified to pH 7 with ammonia, keeping the temperature at 10° C. or below. The organic phase was separated and triturated with petroleum ether (3×100 ml) and the solvent decanted each time. The residual thick oil was dissolved in methylene chloride (240 ml). Sodium bicarbonate (30 g) and water (3 ml) were added. The mixture was cooled to −5° C. D(−) phenylglycyl chloride hydrochloride (37.2 g) was added and the mixture was stirred for 2 hours at 0° C. The mixture was filtered from solids, methylene chloride was evaporated. Butyl acetate (240 ml) and isopropanol (30 ml) were added. Bacampicillin crystallized slowly at 0° C. The solid was filtered, washed and dried. The yield of bacampicillin was 68.2 g.

EXAMPLE 7

To 1-bromoethyl ethyl carbonate (145.8 g) in acetone (720 ml) at 35° C. was added sodium bicarbonate (160 g) and Ampicillin Dane potassium salt (240 g). The suspension was heated at 40° C. for 5 hours. Water (720 ml) was then added and stirring continued for an additional hour, when ethyl acetate (720 ml) was added. The organic layer was separated and washed with 20% aqueous sodium chloride (720 ml), then concentrated under reduced pressure (below 35° C.) to a thick residue.

To the residue was added acetone (720 ml), water (24 ml) and then dropwise a solution of conc. HCl (36 ml) diluted with water (12 ml). An additional amount of HCl (1:1, 7.5 ml) was then added until a constant pH of about 2.2 was obtained. Magnesium Sulphate (40 g) was then added, stirred for 10 minutes and filtered. To the solution was added butyl acetate (400 ml), evaporated in vacuo to remove acetone and butyl acetate (about 320 ml). The residue was diluted with butyl acetate (880 ml) and part of the solvent evaporated under reduced pressure.

The solid was filtered off, washed with butyl acetate (120 ml) and ethyl acetate (120 ml), dried at 40° in vacuo, giving pure bacampicillin hydrochloride. The product conforms with U.S. pharmacopea.

EXAMPLE 8

A mixture of ampicillin trihydrate (15 g), methylaceto acetate (5.65 g), triethylamine (4.05 g) and acetone (7.5 ml) was stirred at 40° C. for 3 hours. Acetone (30 ml) and sodium bicarbonate (12.4 g) were added. 1-Bromoethyl ethyl carbonate (14.6 g) was added dropwise during 1 hour. Stirring was continued at 40° C. for 1 hour. Water (37.5 ml) was added and the reaction was stirred at 20° C. for 1 hour. Ethyl acetate (37.5 ml) was added and the phases separated. The organic phase was washed with 20% sodium chloride solution. Acetone (7.5 ml) was added and a solution of ca. 16% hydrochloric acid was added slowly until a stable pH of 2.2 was obtained. The addition takes 1½–2 hours. The solution was dried over anhydrous sodium sulfate and filtered. Butyl acetate (45 ml) was added and the solution was evaporated in vacuo to remove most of the solvents (bath temperature 35° C.). More butyl acetate (50 ml) was added and partially distilled. The resulting slurry was cooled for several hours and filtered to give 11.6 g bacampicillin.

EXAMPLE 9

A mixture of ampicillin Dane potassium salt (45.6 g), 1-bromoethyl ethyl carbonate (36.0 g), sodium bicarbonate (38.4 g) and acetonitrile (260 ml) is stirred for 3 hours at 40° C. The mixture is filtered and the cake is washed with acetonitrile (2×20 ml). Water (20 ml) is added and the mixture is stirred for 1 hour. Most of the solvent is removed by evaporation at 35°–40° C., under reduced pressure. Acetone (70 ml) and water (4.5 ml) are added. A mixture of concentrated hydrochloric acid (6.85 ml) and water (2.3 ml) is added slowly in order to keep the pH at 2–2.5. If, at the end, the pH is not stable, a small additional amount of 1:1 hydrochloric acid is added until a stable pH in the range 2–2.5 is obtained. The solution is dried and filtered. Butyl acetate (180 ml) and the solution is distilled under reduced pressure to a volume of ca. 40 ml. More butyl acetate (270 ml) is added and the product is allowed to crystallize at ca. 5° C. The mixture is filtered to give 32.5 g bacampicillin.

EXAMPLE 10

Ampicillin Dane potassium salt (30.0 g), sodium bicarbonate (20.0 g), 1-bromoethyl ethyl carbonate (16.9 g) and acetone (90 ml) were stirred at 40° for 5 hours. The reaction mixture was cooled to room temperature and ethyl acetate (90 ml) and 20% sodium chloride solution (100 ml) were added. The mixture was filtered and the phases separated. The organic layer was dried and concentrated. Final concentration under high vacuum gave the 1′-ethoxycarbonyloxy ethyl ester of ampicillin Dane salt (ADS). An analytical sample was crystallized from ether. The compound was characterized by its NMR and IR spectra.

We claim:
1. A process for the preparation of 1′-ethoxycarbonyloxy ethyl benzyl penicillinate having the formula:

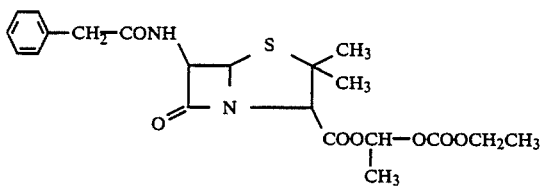

wherein benzyl penicillin having the formula:

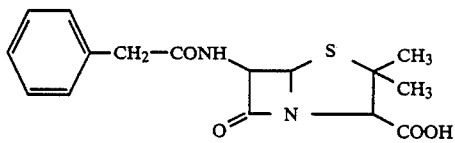

or a salt thereof, is reached with 1-bromoethyl ethyl carbonate:

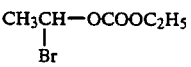

in a non-hydroxylic polar solvent at a temperature of from 20° C. to 50° C.

2. A process according to claim 1, characterized in that the potassium salt of benzyl penicillin is reacted with 1-bromoethyl ethyl carbonate in acetone at a temperature of 35° C. to 45° C.

3. A process according to claim 1 wherein the reaction is carried out at 40° C.

4. A process according to claim 1 wherein the reaction is carried out in the presence of a catalytic amount of tetrabutyl ammonium bromide.

* * * * *

UNITED STATES PATENT AND TRADEMARK OFFICE
CERTIFICATE OF CORRECTION

PATENT NO. : 4,889,929

DATED : December 26, 1989

INVENTOR(S) : Jacob Vaya, et al.

It is certified that error appears in the above-identified patent and that said Letters Patent is hereby corrected as shown below:

col. 1, line 13 and line 18, "Ampicillin" should read -- Ampicillin --;

col. 3, line 63, "o-position" should read -- α-position --;

col. 4, line 8, "ethanol yields.BEC" should read -- ethanol yields BEC. --;

col. 5, line 46, ""ampicillin Dane salt"." should read -- "ampicillin Dane salt": --;

col. 5, line 58, "dichloromethate," should read -- dichloromethane, --;

col. 6, line 56, "A=phehoxy" should read -- A=phenoxy --;

col. 7, line 39, "7-ethoxycarbonyloxy" should read -- 1-ethoxycarbonyloxy --;

col. 8, line 6, "atmospheric pressure" should read -- atmospheric pressure. --;

Signed and Sealed this

Thirtieth Day of June, 1992

Attest:

DOUGLAS B. COMER

*Attesting Officer*     *Acting Commissioner of Patents and Trademarks*